(12) United States Patent
Kiselev et al.

(10) Patent No.: US 9,308,270 B2
(45) Date of Patent: Apr. 12, 2016

(54) PHARMACEUTICAL COMPOSITION ON THE BASIS OF NANOMICELLES CONTAINING EPIGALLOCATECHIN GALLATE AND A METHOD OF ADMINISTRATION THEREOF TO TREAT ATOPIC DERMATITIS, CROHN'S DISEASE, ADENOMYOSIS, AND HYPERPLASTIC DISEASES OF THE PROSTATE GLAND

(71) Applicant: NORDIC LABS LIMITED, Lanarkshire (GB)

(72) Inventors: Vsevolod Ivanovich Kiselev, Moscow (RU); Irina Gennadievna Vasilyeva, Moscow (RU)

(73) Assignee: NORDIC LABS LIMITED, Newhouse, Lanarkshire (GB)

( * ) Notice: Subject to any disclaimer, the term of this patent is extended or adjusted under 35 U.S.C. 154(b) by 0 days.

(21) Appl. No.: 14/263,011

(22) Filed: Apr. 28, 2014

(65) Prior Publication Data

US 2014/0235708 A1   Aug. 21, 2014

Related U.S. Application Data

(63) Continuation-in-part of application No. PCT/RU2012/000625, filed on Jul. 31, 2012.

(30) Foreign Application Priority Data

Oct. 31, 2011 (RU) ................................. 2011143943

(51) Int. Cl.
*A61K 47/34* (2006.01)
*A61K 31/353* (2006.01)
*A61K 9/00* (2006.01)
*A61K 47/10* (2006.01)
*A61K 9/107* (2006.01)

(52) U.S. Cl.
CPC .............. *A61K 47/34* (2013.01); *A61K 9/0053* (2013.01); *A61K 9/1075* (2013.01); *A61K 31/353* (2013.01); *A61K 47/10* (2013.01)

(58) Field of Classification Search
CPC ..... A61K 31/35; A61K 31/353; A61K 47/34; C07D 311/58
USPC .......................................... 514/456; 429/729
See application file for complete search history.

(56) References Cited

U.S. PATENT DOCUMENTS 8,143,308 B2 *  3/2012  Bruno et al. .................. 514/456
2011/0189316 A1   8/2011  Song et al.

FOREIGN PATENT DOCUMENTS

JP    11080693 A    3/1999
RU    2377984 C2    1/2010

OTHER PUBLICATIONS

International Search Report of PCT/RU2012/000625, dated Apr. 18, 2013.
Hirofumi Tachibana (2011), "Green Tea Polyphenol Sensing," Proc. Jpn. Acad., 87, 66-80.
Nurulain T. Zaveri (2006), "Green Tea and its Polyphenolic Catechins: Medicinal Uses in Cancer and Noncancer Applications," Life Sciences, 78, 2073-2080.
Li S., Hattori T., Kodama E.N. (2011), "Epigallocatechin Gallate Inhibits the HIV Reverse Transcription Step," Antivir. Chem. Chemother., 21(6), 239-243.
Cheng H.Y., Lin C.C., Lin T.C. (2002), "Antiviral Properties of Prodelphinidin B-2 3,-O-Gallate from Green Tea Leaf," Antivir. Chem. Chemother., 13 (4), 223-229.
Song J.M., Lee K.H., Seong B.L. (2005) "Antiviral Effect of Catechins in Green Tea on Influenza Virus," Antiviral Res., 68 (2), 66-74.
Kang W.S., Lim I.H., Yuk D.Y., Chung R.Y., Park J.B., Yoo H.S., Yun Y.P. (1999), "Antithrombotic Activities of Green Tea Catechins and Epigallocatechins Gallate," Thromb. Res., 96 (3), 229-237.
Sah J.F., Balasubramanian S., Eckert R.L., Rorke E.A. (2004), "Epigallocatechin-3-gallate Inhibits Epidermal Growth Factor Receptor Signaling Pathway," J. Biol. Chem., 279, 12755-12762.
Masuda M., Suzuki M., Lim J.T.E., Weinstein I.B. (2003), "Epigallocatechin-3-gallate Inhibits Activation of HER-2/neu and Downstream Signaling Pathways in Human Head and Neck and Breast Carcinoma Cells," Clin. Cancer Res., 9, 3486-3491.
Sylvie Lamy, Denis Gingras, Richard Béliveau (2002), "Green Tea Catechins Inhibit Vascular Endothelial Growth Factor Receptor Phosphorylation," Cancer Res., 62, 381-385.
Yang C.S., Landau J.M., Huang M.T., Newmark H.L. (2001) "Inhibition of Carcinogenesis by Dietary Polyphenolic Compounds," Annu. Rev. Nutr., 21, 381-406.
Fujiki H., Suganuma M., Okabe S., et al. (1996) "Japanese Green Tea as a Cancer Preventive in Humans," Nutrition Reviews, 54 (11), S67-S70.
Naghma Khan, Farrukh Afaq, Mohammad Saleem, Nihal Ahmad, and Hasan Mukhtar (2006), "Targeting Multiple Signaling Pathways by Green Tea Polyphenol Epigallocatechin-3-Gallate," Cancer Res, 66 (5).
H.-H. Sherry Chow, Yan Cai, David S. Alberts, et al. (2001), "Phase I Pharmacokinetic Study of Tea Polyphenols following Single-dose Administration of Epigallocatechin Gallate and Polyphenon E," Cancer Epidemiol. Biomarkers Prev., 10, 53-58.

(Continued)

*Primary Examiner* — Kristin Vajda
(74) *Attorney, Agent, or Firm* — Collard & Roe, P.C.

(57) ABSTRACT

The invention relates to pharmacy. It is an object of the present invention to produce nanomicellar structures containing EGCG and achieving a positive result consisting in increasing bioavailability in peroral administration. The object of this invention is achieved by a new pharmaceutical composition for peroral administration containing epigallocatechin-3-gallate as the active component and a target additive that is a block copolymer of oxyethylene and oxypropylene, in which the content of the hydrophobic block is less than 50% by mass and the hydrophilic block has a molecular weight of 2,250 daltons or more at a ratio of the block copolymer to the active component ranging from 1:1 to 10:1. The composition improves absorption of the active compound by the blood flow when delivered perorally.

6 Claims, 2 Drawing Sheets

(56) References Cited

OTHER PUBLICATIONS

Imtiaz a. Siddiqui, Vaqar M. Adhami, Dhruba J. Bharali, Bilal B. Hafeez, Mohammad Asim, Sabih I. Khwaja, Nihal Ahmad, Huadong Cui, Shaker A. Mousa, and Hasan Mukhtar (2009), "Introducing Nanochemoprevention as a Novel Approach for Cancer Control: Proof of Principle with Green Tea Polyphenol Epigallocatechin-3-Gallate," Cancer Res., 69(5), 1712-1716.
Kristin R. Landis-Piwowar, Congde Huo, Di Chen, Vesna Milacic, Guoqing Shi, Tak Hang Chan and Q. Ping Dou (2007), "A Novel Prodrug of the Green Tea Polyphenol Epigallocatechin-3-Gallate as a Potential Anticancer Agent," Cancer Res., 67, 4303-4310.
Jia-You Fang, Woan-Ruoh Lee, Shing-Chuan Shen, Yen-Ling Huang (2006), "Effect of Liposome Encapsulation of Tea Catechins on their Accumulation in Basal Cell Carcinomas," Journal of Dermatological Science, 42, 101-109.
Adam Smith, Brian Giuntac, Paula C. Bickford, Michael Fountaine, Jun Tana, and R. Douglas Shytle (2010), "Nanolipidic Particles Improve the Bioavailability and α-Secretase Inducing Ability of Epigallocatechin-3-Gallate (EGCG) for the Treatment of Alzheimer's Disease," International Journal of Pharmaceutics, 389, 207-212.
Foster B (V)., Cosgrove T., Hammouda B. (2009), "Pluronic Triblock Copolymer Systems and their Interactions with Ibuprofen," Langmuir, 25(12), 6760-6766.
Jerry McLarty, Rebecca L.H. Bigelow, Mylinh Smith, et al. (2009) "Tea Polyphenols Decrease Serum Levels of Prostate-Specific Antigen, Hepatocyte Growth Factor, and Vascular Endothelial Growth Factor in Prostate Cancer Patients and Inhibit Production of Hepatocyte Growth Factor and Vascular Endothelial Growth Factor in vitro," Cancer Prey. Res., 2 (7), 673-681.
Lambert, Joshuah D. et al., (2005) "Inhibition of carcinogenesis by polyphenols: evidence from laboratory investigations" Am J. Clin 2005: 81 (suppl) 284S-291S.
Product Information—Epigallocatechin Gallate, Item No. 70935, Cayman Chemical, Sep. 4, 2014, 1 page, https://www.caymanchem.com/pdfs/70935.pdf.
Cai et al., Contribution of Presystemic Hepatic Extraction to the Low Oral Bioavailability of Green Tea Catechins in Rats, Drug Metabolism and Disposition, Nov. 1, 2011, vol. 30, No. 11, (Abstract) 2 pages, http://dmd.aspetjournals.org/content/30/11/1246.short.
Ibuprofen, Compound Summary for CID 3672, PubChem Open Chemistry Database, U.S. National Library of Medicine, 84 pages, http://pubchem.ncbi.nlm.nih.gov/compound/ibuprofen/#section=Top, 2015.
Luckow et al., Comparative Biological Availability of Two Different Ibuprofen Granules, PubMed Commons, Nov. 1992, 42(11), (Abstract) 2 pages, http://www.ncbi/nlm.nih.gov/pubmed/1492847.
Dewland et al., Bioavailability of Ibuprofen Following Oral Administration of Standard Ibuprofen, Sodium Ibuprofen or Ibuprofen Acid Incorporating Poloxamer in Healthy Volunteers, BMC Pharmacology & Toxicology, 2009, 6 pages, http://www.biomedcentral.com/1472-6904/9/19.

\* cited by examiner

PHARMACEUTICAL COMPOSITION ON THE BASIS OF NANOMICELLES CONTAINING EPIGALLOCATECHIN GALLATE AND A METHOD OF ADMINISTRATION THEREOF TO TREAT ATOPIC DERMATITIS, CROHN'S DISEASE, ADENOMYOSIS, AND HYPERPLASTIC DISEASES OF THE PROSTATE GLAND

CROSS REFERENCE TO RELATED APPLICATIONS

Applicants claim priority under 35 U.S.C. §119 of Russian Application No. 2011143943 filed Oct. 31, 2011, Applicants also claim priority and this application is a continuation-in-part under 35 U.S.C. §120 of International Application No. PCT/RU2012/000625 filed Jul. 31, 2012, which claims priority under 35 U.S.C. §119 of Russian Application No. 2011143943 filed Oct. 31, 2011. The International Application under PCT article 21(2) was not published in English. The disclosures of the aforesaid International Application and Russian Application are incorporated herein by reference.

FIELD OF THE INVENTION

The invention relates to pharmacy and, in particular, to new pharmaceutical compositions for peroral delivery of epigallocatechin-3-gallate (EGCG) and to methods for treating diseases with the help thereof.

BACKGROUND OF THE INVENTION

The role of compounds of plant origin in developing new medicinal preparations has evoked unprecedented interest in recent years. It is dealt with in numerous studies that have identified compounds showing a broad spectrum of biological activities, such as flavonoids, flavins, and catechins, among others.

By far the greatest interest has been raised lately by green tea polyphenols, most of them catechins exhibiting a wide spectrum of protective effects. Aqueous extract of green tea contains epigallocatechin-3-gallate (EGCG), epigallocatechin (EGC), epicatechin-3-gallate (ECG), and epicatechin (EC).

It is common knowledge that EGCG as an antioxidant is 100 time more effective than vitamin C and 25 as effective as vitamin E (α-tocopherol). The antioxidant qualities of catechins derive from their chemical origin, specifically, a multitude of hydroxyl groups turning these compounds into molecular traps for free radicals that damage the structure of the cell DNA and the cell membranes. In fact, this is the primary quality that drew close attention to EGCG as a biologically active substance. To this day, the capacity of EGCG and other tea catechins to protect healthy cells from oxidative stress is one of the much studied subjects.

Powerful anti-proliferative potential is a further important quality of EGCG targeted at all cells that stimulate expression of signal cascades on which the growth and number of cells of a particular type depends. Modulation of these processes by catechins turns them into powerful anti-inflammatory, anti-proliferative, and anti-angiogenic natural components (Hirofumi Tachibana (2011), "Green Tea Polyphenol Sensing," *Proc. Jpn. Acad.*, 87, 66-80; Nurulain T. Zaveri (2006), "Green Tea and its Polyphenolic Catechins: Medicinal Uses in Cancer and Noncancer Applications," *Life Sciences*, 78, 2073-2080).

Maximum possible tea drinking during the day results in EGCG concentration increasing to 326 ng/ml in human plasma. EGCG semi-ejection time is between 5 and 5.5 hours, much longer than it is for other catechins. Side effects from intake of epigallocatechins begin to show up at very large doses in excess of grams.

Numerous studies are presently carried out to explore the properties and effects of green tea catechins. For example, data were produced a short while ago on the antiviral activity of green tea catechins relative to various viruses. Activity of catechins was studied in respect of herpes simplex viruses, adenoviruses, flu viruses, and human immunodeficiency viruses (Li S., Hattori T., Kodama E. N. (2011), "Epigallocatechin Gallate Inhibits the HIV Reverse Transcription Step," *Antivir. Chem. Chemother.*, 21(6), 239-243).

It was demonstrated that catechins in in vitro systems suppress significantly the infective activity of the herpes simplex virus, mostly at the stage of virus attachment and penetration into the host cell, and also at later stages of viral infection (Cheng H. Y., Lin C. C., Lin T. C. (2002), "Antiviral Properties of Prodelphinidin B-2 3,-O-Gallate from Green Tea Leaf," *Antivir. Chem. Chemother.*, 13 (4), 223-229).

In respect of flu infection, Korean researchers published recently their findings on antiviral activity of green tea catechins against the viruses of flu A (H1N1 and H3N2) and flu B. Their studies have shown the hemagglutinin inhibiting activity of some catechins, among which the effect of epigallocatechin was most pronounced. Epigallocatechin altered the physical properties of the viral membrane in MDSC cells, interfering with the life of the virus, suppressing synthesis of the viral RNA, and inhibiting neuraminidase activity. In other words, it actually was active at all stages of infection (Song J. M., Lee K. H., Seong B. L. (2005) "Antiviral Effect of Catechins in Green Tea on Influenza Virus," *Antiviral Res.*, 68 (2), 66-74). Similar data on antiviral activity of epigallocatechin were obtained at the Influenza Research Institute, Russian Academy of Medical Sciences, in in vitro systems. Work now continues to study the mechanisms of antiviral activity of epigallocatechin and conduct research on animal models.

In addition, data were obtained on antithrombotic activity of catechins. In this respect, epigallocatechin is the most active catechin of all (Kang W. S., Lim I. H., Yuk D. Y., Chung R. Y., Park J. B., Yoo H. S., Yun Y. P. (1999), "Antithrombotic Activities of Green Tea Catechins and Epigallocatechins Gallate," *Thromb. Res.*, 96 (3), 229-237), a quality that is extremely important for treating flu because the pathogenic mechanisms of flu infection development are known to affect the vascular system and consequent aggregation of thrombocytes that, in turn, causes frequent flu complications such as infarctions and strokes.

It is held to be a proven fact today that the anti-inflammatory activity of EGCG is based on its capacity to block cytokine-dependent pathways of stimulation of pathological cell proliferation.

Mention must also be made of the capacity of EGCG to increase the general immune reactivity of the organism.

Understandably, the general immune status is very important for full-scale anti-inflammatory reaction in any organ or tissue, and disruption of immune response is a key component in the pathogenesis of many hyperplastic and infectious diseases, The immunomodulating properties of EGCG consist, first, in normalizing the pathological immune response of the organism, in particular, during allergic reactions. Besides, EGCG restores the balance of Th1 and Th2 subtypes of T-helper lymphocytes that have an important part in the immune response (V. I. Kiselev, A. A. Liashenko (2005), "Molecular Mechanisms Regulating Hyperplastic Processes," Dimitrade Graphic Group Publishers, Moscow).

Anti-inflammatory activity of EGCG is, however, only one of the numerous biological activities of this compound.

Another critical property of EGCG is its capacity, on the one hand, to suppress pathological cell growth caused indirectly by polypeptide growth factors (in particular, epidermal growth factor) and, on the other hand, set off selective apoptosis of cells having an abnormally high proliferative activity. EGCG is, therefore, a powerful blocker of hyperplastic processes in epithelial tissues of different origins (Sah J. F., Balasubramanian S., Eckert R. L., Rorke E. A. (2004), "Epigallocatechin-3-gallate Inhibits Epidermal Growth Factor Receptor Signaling Pathway," *J. Biol. Chem.*, 279, 12755-12762; Masuda M., Suzuki M., Lim J. T. E., Weinstein I. B. (2003), "Epigallocatechin-3-gallate Inhibits Activation of HER-2/neu and Downstream Signaling Pathways in Human Head and Neck and Breast Carcinoma Cells," *Clin. Cancer Res.*, 9, 3486-3491).

In addition, EGCG expressly slows down the pathological growth of blood vessels (pathological neoangiogenesis), a process that frequently accompanies hyperplastic processes (Sylvie Lamy, Denis Gingras, Richard Beliveau (2002), "Green Tea Catechins Inhibit Vascular Endothelial Growth Factor Receptor Phosphorylation," *Cancer Res.*, 62, 381-385).

As the situation is today, the onto-protective properties of EGCG may be considered proven as a fact and well documented in studies. Also established reliably is the capacity of EGCG to block molecular mechanisms causing pathological increase in the number of cells (pathological proliferation), pathological neoangiogenesis (growth of vessels), and rise in invasive activity of transformed cells. By now, a large number of molecular targets inhibited by EGCG and causing indirectly all stages of the pathogenesis of hyperplastic processes and malignant growth have been identified. Biological activity of EGCG and other tea catechins has been shown in experimental, clinical, and large-scale epidemiological studies in respect of a vast number of pre-tumorous and tumorous diseases of the mammary gland, ovaries, cervix of the uterus, endometrium, prostate, skin, gastrointestinal tract (mouth, esophagus, stomach, small and large intestines, liver, and pancreas), and lungs (Yang C. S., Landau J. M., Huang M. T., Newmark H. L. (2001) "Inhibition of Carcinogenesis by Dietary Polyphenolic Compounds," *Annu. Rev. Nutr.*, 21, 381-406; Fujiki H., Suganuma M., Okabe S., et al. (1996) "Japanese Green Tea as a Cancer Preventive in Humans").

A majority of observations confirming the wide spectrum of biological properties of epigallocatechins has been made in in vitro experiments. Maximum activity of EGCG in experiments with cell lines was recorded at concentrations of 10 to 50 µm (Naghma Khan, Farrukh Afaq, Mohammad Saleem, Nihal Ahmad, and Hasan Mukhtar (2006), "Targeting Multiple Signaling Pathways by Green Tea Polyphenol Epigallocatechin-3-Gallate," *Cancer Res*, 66 (5)).

While the maximum concentration of EGCG in the plasma of patients taking preparations containing green tea catechins did not exceed 1 µm, higher doses caused side effects, without, however, affecting significantly the content of EGCG in blood (H.-H. Sherry Chow, Yan Cai, David S. Alberts, et al. (2001), "Polyphenon E Single-dose Administration of Epigallocatechin Gallate and Phase I Pharmacokinetic Study of Tea Polyphenols Following," *Cancer Epidemiol. Biomarkers Prev.*, 10, 53-58).

Researchers studying the pharmacokinetics of EGCG reach the conclusion that the above effect is due to the low bioavailability of catechins. According to various sources, bioavailability of catechins is not higher than 1%. Because of this bioavailability, peroral use of catechins cannot assure the desired therapeutic level of catechins in target organs and hence a steady curative effect. For this reasons, many attempts are being made to achieve improvements in the catechin effect by developing various catechin-based formulations (Imtiaz A. Siddiqui, Vaqar M. Adhami, Dhruba J. Bharali, Bilal B. Hafeez, Mohammad Asim, Sabih I. Khwaja, Nihal Ahmad, Huadong Cui, Shaker A. Mousa, and Hasan Mukhtar (2009), "Introducing Nanochemoprevention as a Novel Approach for Cancer Control: Proof of Principle with Green Tea Polyphenol Epigallocatechin-3-Gallate," *Cancer Res.*, 69(5), 1712-1716; Kristin R. Landis-Piwowar, Congde Huo, Di Chen, Vesna Milacic, Guoqing Shi, Tak Hang Chan and Q. Ping Dou (2007), "A Novel Prodrug of the Green Tea Polyphenol Epigallocatechin-3-Gallate as a Potential Anticancer Agent," *Cancer Res.*, 67, 4303-4310).

These inventors have demonstrated that EGCG incorporated into nanoparticles on the basis of lactic acid polymers and polyethylene glycol has the same pharmacological activity in doses approximately 10% of the doses of free EGCG and above that of preparations that are not part of formulations. These data were reproduced on cell lines and also on in vivo models when the preparation was administered intraperitoneally. The data obtained give certainty to assumptions that increasing bioavailability causes a significant increase in biological effects. The researchers, though, do not cite any data to show that an increase in the dose of nano-encapsulated EGCG helps make the preparation pharmacologically active in comparison with free EGCG. Furthermore, their invention has a significant deficiency owned up to by the inventors themselves. Actually, the polymers used in their study are very unstable in the acidic medium of the stomach, so much so that they have to be used in injections only. An attempt was made to use a liposome form of EGCG (Jia-You Fang, Woan-Ruoh Lee, Shing-Chuan Shen, Yen-Ling Huang (2006), "Effect of Liposome Encapsulation of Tea Catechins on their Accumulation in Basal Cell Carcinomas," *Journal of Dermatological Science*, 42, 101-109). This composition, though, produced a positive effect when used externally and subcutaneously only.

These inventors consider a recent pharmaceutical composition on the basis of lipidic particles that help to almost double the oral bioavailability of EGCG (Adam Smith, Brian Giuntac, Paula C. Bickford, Michael Fountaine, Jun Tana, and R. Douglas Shytle (2010), "Nanolipidic Particles Improve the Bioavailability and α-Secretase Inducing Ability of Epigallocatechin-3-Gallate (EGCG) for the Treatment of Alzheimer's Disease," *International Journal of Pharmaceutics*, 389, 207-212) to be the closest related prior art of their invention. Doubling bioavailability, though, is incapable of tapping the pharmaceutical potential of EGCG in full measure. For this reason, it is still a priority to develop EGCG formulations that increase EGCG bioavailability and are suitable for peroral use.

SUMMARY OF THE INVENTION

It is an object of this invention is to produce nano-micellar structures containing EGCG and increasing bioavailability upon peroral application as their positive result.

This object is achieved by a new pharmaceutical composition for peroral application that contains epigallocatechin-3-gallate as an active component and a target additive that is a block copolymer of oxyethylene and oxypropylene, wherein the content of the hydrophobic block is at least 50% by mass and the hydrophilic block has a molecular weight of 2,250 daltons or more, at a mass ratio of the block copolymer to the active component ranging from 1:1 to 10:1.

Furthermore, the composition may contain Pluronic F127 as a block copolymer of oxyethylene and oxypropylene.

Also, the pharmaceutical composition may contain a pharmaceutically acceptable carrier as an additional ingredient.

Finally, the pharmaceutical composition may take the form of a tablet, or lyophilized powder, or suspension, or a capsule.

The claimed object is also achieved by a method of administration of the above pharmaceutical composition to treat atopic dermatitis, Crohn's disease, adenomyosis, and hyperplastic diseases of the prostate gland.

The block copolymers of oxyethylene and oxypropylene used in the claimed composition are also known under the name of Pluronic or Poloxamer.

The hydrophobic-hydrophilic properties of Pluronics and their capacity to solubilize water-insoluble compounds depend on the size and ratio of polyoxyethylene (hydrophilic) to polyoxypropylene (hydrophobic) blocks of the polymer. Although these block copolymers are used widely in pharmaceutical and cosmetic compositions for purposes including increasing solubility of hydrophobic water-insoluble compounds (Foster B., Cosgrove T., Hammouda B. (2009), "Pluronic Triblock Copolymer Systems and their Interactions with Ibuprofen," *Langmuir*, 25(12), 6760-6766), individual decision is needed on their use in each specific drug.

An analysis of EGCG solubility in Pluronics containing different proportions of hydrophobic and hydrophilic blocks has shown that polymers containing 50% or more by mass of the hydrophobic block have a higher solubilizing capacity than polymers containing under 50% by mass of the hydrophilic block. It is a well-known fact that the hydrophobic block of some Pluronics has a constant molecular weight, while the weight of the percentage-wise content of the polyoxyethylene block tends to vary.

Surprisingly, EGCG bioavailability turned out to depend on the molecular weight of the hydrophilic block as well. A higher bioavailability is attributed to block copolymers of oxyethylene and oxypropylene in which the content of the hydrophobic block is less than 50% by mass and the hydrophilic block has a molecular weight of 2,250 daltons or more. Pluronic F127 has proved to have the greatest effect sufficient to produce stable aqueous dispersions containing more than 50 mg/ml of EGCG. Peroral administration of this EGCG composition to rats increased significantly (more than tenfold) the bioavailability of EGCG as a systemic exposition to the preparation. The weight ratio of a selected block copolymer to the active component may be varied depending on the desired release time within 10:1 to 1:1, on average. The most optimal ratio for the Pluronic and EGCG was found to be 1.5:1.

Compositions according to this invention may be obtained, for example, by joint or separate dissolution of components in suitable solvents such as water, alcohol, or water-alcohol solutions and then mixing the solutions produced in desired proportions.

The resultant solutions may then be combined and dried to yield a solid medicinal form. They are dried by any technologically suitable method or a combination of methods, including, but not limited to, methods such as evaporation on a rotary evaporator or SpeedVac, lyophilic drying, or continuous flow drying.

Ready medicinal forms may be obtained by shaping the dried compositions into tablets using appropriate excipients, for example, sodium stearate, lactose, or cellulose derivatives.

Ready medicinal forms may be produced by packing the dried composition into capsules, for example, gelatin capsules having a solid shell.

The present invention also relates to methods for treating diseases by the claimed pharmaceutical compositions containing an effective quantity of EGCG.

Considering the above molecular targets of EGCG, specifically, restoration of apoptosis processes, antiproliferative, anti-tumor and anti-angiogenic activity, and antiviral activity, the compositions described herein are intended for treating proliferative diseases such as myoma of the uterus, adenomyosis, and hyperplastic diseases of the prostate gland.

The effective quantity of epigallocatechin-3-gallate needed for treatment and prophylaxis may vary depending on the type and severity of the disease, age and state of the patient, and may be determined by the doctor in charge in each specific case. The doses used vary within the range of 2 to 2,000 mg a day.

BRIEF DESCRIPTION OF THE DRAWINGS

The invention is illustrated in the accompanying drawings wherein.

DESCRIPTION OF THE EMBODIMENTS OF THE INVENTION

Figure 1:
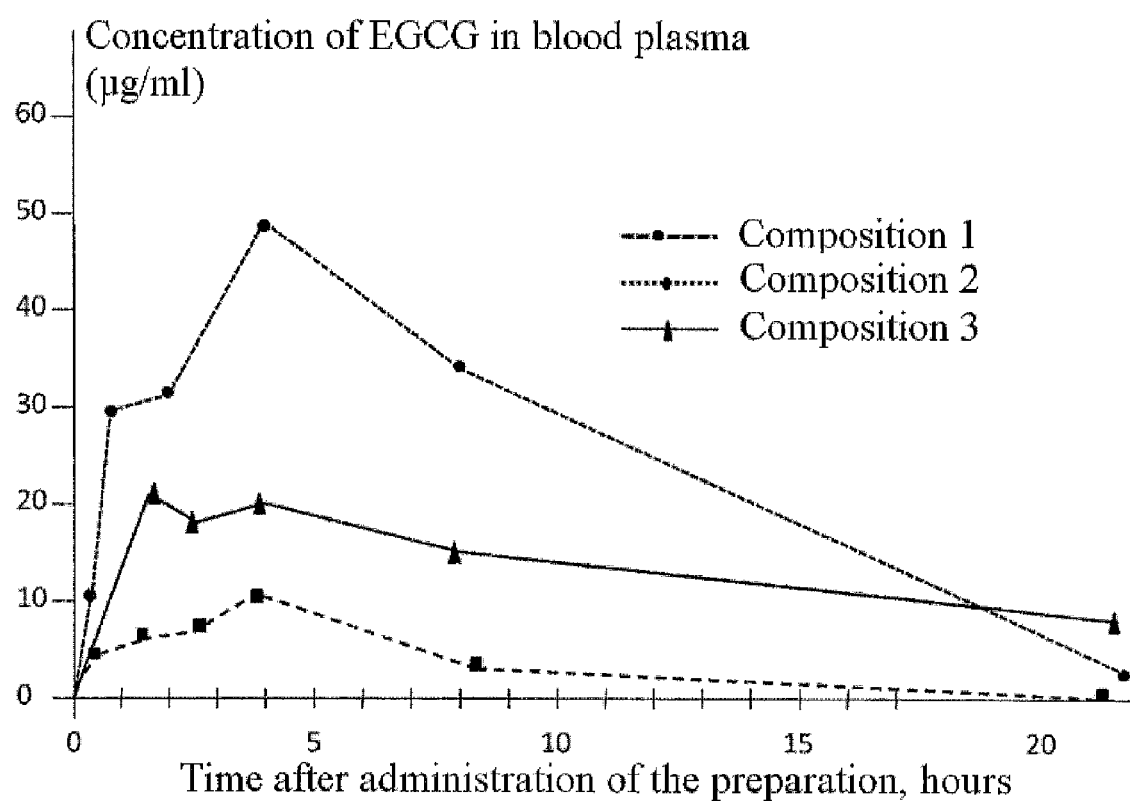
FIG. 1 is a view of curves showing dependence of EGCG concentration in rat plasma on the time elapsing after drug application for three compositions:
Composition 1: EGCG—500 mg/kg;
Composition 2: EGCG/F127—500 mg/kg; and
Composition 3: EGCG/F127—100 mg/kg.

The invention is also illustrated by the following examples:

Example 1

Preparation of an EGCG Composition with Pluronic F127 for Solubility Studies 50 mg of EGCG were dissolved in 1 ml of alcohol-water solution (97/3 by volume) containing different concentrations of Pluronic F127. The resultant mixture was incubated at 20° to 25° C. for 30 minutes at constant stirring. Ethanol was evaporated, and the resultant formulation was dried in high vacuum. The dried sample was suspended in distilled water, incubated at room temperature for 30 minutes, filtered off, and EGCG was determined by the HPLC method as described in Example 5. To be noted, samples of free EGCG (containing 90% of catechin) studied in these experiments had water solubility of 0.48 mg/ml. The results of the experiments are shown in Table 1.

TABLE 1

Solubility of EGCG in Water-Alcohol Solutions Having Different Content of F127

| EGCG (mg/ml) | F127 (%), weight/volume | EGCG (mg/ml) |
|---|---|---|
| 50 | 2 | 0.87 |
| 50 | 4 | 7.24 |

TABLE 1-continued

Solubility of EGCG in Water-Alcohol Solutions Having Different Content of F127

| EGCG (mg/ml) | F127 (%), weight/volume | EGCG (mg/ml) |
|---|---|---|
| 50 | 6 | 16.37 |
| 50 | 8 | 43.88 |

As follows from the results obtained, solubility of EGCG in 8% Pluronic F127 was 105 times that in water.

Example 2

Preparation of EGCG Composition with Pluronic F127 for Oral Delivery (50 Mg/Kg Dose)

25 mg of EGCG were dissolved in 1 ml of ethanol, and the resultant solution was then mixed with 1 ml of 5% (weight-volume) of Pluronic F127 solution in an alcohol-water solution (97/3 by volume). The solution was incubated at room temperature for 30 minutes at constant stirring. Ethanol was evaporated, and the resultant formulation was dried in high vacuum. The control EGCG preparation was obtained by suspending EGCG in distilled water at a concentration of 25 mg/ml.

Example 3

Preparation of an EGCG Composition with Pluronic F127 for Oral Administration (100 Mg/Kg Dose)

37.5 mg of EGCG were dissolved in 1 ml of ethanol and the resultant solution was mixed with 1 ml of 6% (weight-volume) solution of Pluronic F127 in an alcohol-water solution (97/3 by volume). The solution was incubated at room temperature for 30 minutes at constant stirring. Ethanol was evaporated, and the resultant formulation was dried in high vacuum. A control EGCG preparation was obtained by suspending EGCG in distilled water at a concentration of 25 mg/ml.

Example 4

Preparation of an EGCG Composition with Pluronic F127 for Oral Administration (500 Mg/Kg Dose)

50 mg of EGCG were dissolved in 1 ml of ethanol and the resultant solution was then mixed with 1 ml of 8% (weight-volume) solution of Pluronic F127 in an alcohol-water solution (97/3 by volume). The solution was incubated at room temperature for 30 minutes at constant stirring. Ethanol was evaporated, and the resultant formulation was dried in high vacuum. A control EGCG preparation was obtained by suspending EGCG in distilled water at a concentration of 50 mg/ml. The substance was suspended at a 200 mg/kg concentration for testing the maximum EGCG concentration (2,500 mg/kg).

Example 5

Pharmacokinetic Studies of Samples Prepared in Examples 3 and 4

Experiments were conducted on laboratory rats of Sprague-Dawley breed weighing between 250 g and 350 g. All studies on animals were conducted in accordance with "Guidelines for Care and Use of Experimental Animals,"

Control EGCG preparations were administered perorally in doses of 100, 500, and 2,500 mg/kg. Samples of EGCG formulations were administered to the animals in doses of 50, 100, and 500 mg/kg. At fixed time intervals (10 and 30 minutes, 1, 1.5, 2, 3, 8, and 24 hours), blood samples were drawn from the animals and, following centrifuging, plasma was drawn from the samples for analysis, refrigerated, and kept at −80° C. until it was needed for studies.

For analytical studies to be conducted, the plasma samples were unfrozen, centrifuged, and divided into aliquots of 0.1 ml each. The samples were extracted three times in 2 ml of ethyl acetate for 5 minutes at constant shaking. Following extraction, the samples were centrifuged at 1,000 r.p.m. for 10 minutes. The supernatant was separated and placed in a glass tube. The organic phase was evaporated and the dry samples were kept at −80° C. until they were needed for chromatographic analysis.

TABLE 2

Pharmacokinetic Profile of EGCG in Rat Plasma

| Group | Formulation | $C_{max}$ µg/ml | Ratio $C_{max}$ Formulation/ Control | $AUC_{0-24\,hr}$ µg · hr/ml | Ratio $AUC_{0-24\,hr}$ Formulation/ Control |
|---|---|---|---|---|---|
| G-1* | Control 2.5 g/kg | 58.6 ± 22.4 | — | 179.2 ± 54.33 | — |
| G-2 | Control 500 mg/kg | 10.65 ± 1.14 | — | 49.23 ± 4.95 | — |
| G-3 | EGCG/ F127 500 mg/kg | 49.34 ± 2.86 | 4.63 | 632.8 ± 57.7 | 12.9 |
| G-4 | EGCG/ F127 100 mg/kg | 21.73 ± 2.50 | | 341.4 ± 19.1 | |

*In group G-1, administration of the dose given in the table resulted in the death of the animals.

In groups G-5 (control 100 mg/kg) and G-6 (EGCG/F127 50 mg/kg), the EGCG concentration level was below LOQ and was not determined.

The results shown in Table 2 suggest the following conclusions:

1. EGCG formulations administered to the animals in a 500 mg/kg dose increased systemic exposition of the substance studied by more than 10 times that of EGCG administered without formulation.

2. The maximum EGCG dose (2,500 mg/kg) administered to the animals without formulation was toxic to the animals. Not a single dose of formulated EGCG, though, caused toxic reactions.

These data are shown graphically in FIG. 1 that is a view of the pharmacokinetic profile of EGCG in rat plasma.

Example 6

Figure 2:
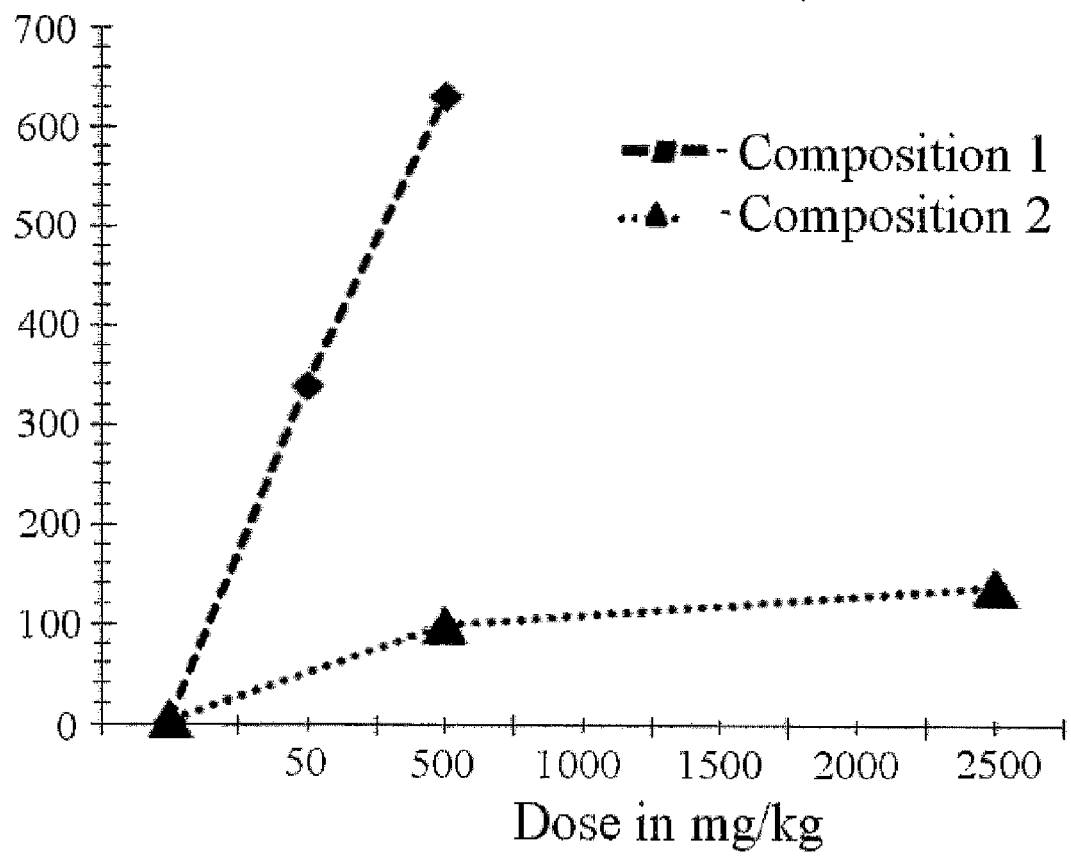
FIG. 2 is a view of curves showing dependence of total EGCG concentration in rat plasma on the EGCG dose for two compositions:
Composition 1: EGCG/F127, and
Composition 2: Control EGCG.

Dependence of EGCG Concentration on Different Doses of Control Preparations and Formulated Preparations The inventors studied dependence of EGCG concentration in rat plasma on the administration of different doses of control preparations and formulated preparations. The results produced show that rising concentration of unformulated EGCG administered to animals had a nonlinear pattern and reached a plateau at the 500 mg/kg dose, while administration of EGCG formulations caused a proportional increase in the concentration in animal plasma. FIG. 2 shows the results of the experiments.

Example 7

Efficiency of the Claimed Preparation in Treatment of Atopic Dermatitis

We observed 52 patients with atopic dermatitis (AD) aged between 18 and 28 years, including 39 men (75%) and 13 women (25%). The skin manifestations of the disease matched the AD clinic having a morphology and rash localization typical of this kind of dermatosis. The patients were found to have the following clinical AD forms: 37 patients (71.2%) had an erythematous-squamous AD with mild or moderate lichenification; nine patients (17.3%) had an eczematous form; five patients (9.6%) had a pruritus-like AD; and one patient (1.9%) had a lichenoid AD. The severity of the disease was assessed by the SCORAD index and varied from 12.2 to 61.5. Of all the patients, 32 (61.5%) had a mild disease, 18 patients (34.6%) had a moderate form of disease, and two patients (3.9%) had a heavy disease form. White developed, diffuse steady dermographism showed up in 46% of the patients. All the patients complained of itching of varying intensity—from insignificant to biopsic. Among them, 42 patients (80.8%) said itching was moderate and tolerable, and ten patients said it was intolerable. A majority of the patients (45, or 86.5%) complained of irritability, low spirits, early fatigue, and disturbed sleep. A majority of the patients (91.9%) had variations in disease dynamics. Most frequently, AD aggravation set in with the onset of the fall-winter period. Among the factors provoking a successive aggravation, 33 patients (63.5%) cited deviation from their hypoallergenic diets, 10 patients (19.2%) named stress situations, six patients (11.5%) attributed it to infectious diseases, and five AD patients (9.6%) put it to medication taking.

The AD patients were treated with a new preparation in which EGCG was the active substance and had a high bioavailability.

The preparation was used in the form of capsules each containing 100 mg of the active substance. All the patients were given one capsule of the preparation three times a day.

The results of therapy were assessed on the basis of changes in the clinical picture on the seventh and 14th days of treatment and a month after the commencement of treatment. Dynamics of the skin symptomatology evaluated on the SCORAD scale served as an objective criterion.

Among the 52 patients who had been given the preparation, clinical recovery manifested in cessation of itching and inflammatory skin changes was registered in 12 patients (23.1%) who had a mild form of disease and in 11 patients (21.1%) who had a disease of medium severity 15 days, on average, from the commencement of treatment. Significant improvement was achieved in 10 patients (19.2%) with a mild form of the disease and in six patients (11.6%) with a medium severity of the disease. Positive dynamics in the form of improvement under the effect of treatment was achieved in eight patients (15.3%) with a mild form and one patient (1.9%) with a severe form of the disease. The treatment had no effect on two patients (3.8%) with a light form and one patient (1.9%) with a medium severity of the disease. The preparation had a clinical efficiency of 75%.

Cytokine Production

Flow cytometry on beads coated with antibodies to cytokines was used to determine the production level of the tumor necrosis factor alpha (TNF-α) and interferon g (IFN-g) in atopic dermatitis patients before and after treatment.

Following treatment, there was a reliable (t-test, $p<0.05$) decrease in the production of TNF-α and IFN-g.

Production of IgE

Treatment with the preparation resulted in a reliable reduction in the IgE level, a relatively rare occurrence for this disease. Another sampling of the patients' blood was taken six weeks to 2 months later. Immunoglobulins in blood serum have a lifetime of around a month. Accordingly, reduction in the IgE level in the AD patients' blood serum after treatment was a sign of direct effect of the preparation on IgE production. IgE was reduced in 100% cases, even if the initial level was low enough.

Example 8

Clinical Efficiency of the New EGCG Formulation for Preventing Relapses of Crohn's Disease Purpose It was the researchers' purpose to determine the efficiency of the new EGCG formulation in maintaining remission in Crohn's disease cases.

Research Structure

The research was a randomized double blind placebo-controlled study one year long.

Patients

The research covered 64 patients (18 to 68 years old, 52% of them men) affected by Crohn's disease in the clinical remission stage with a high risk of relapse. Laboratory data showed a chronic inflammatory process. Exclusion criteria were age under 18 or over 75, taking of mesalamine, sulfasalazine, or corticosteroids over three preceding months, and immunosuppressive preparations, over six preceding months.

Treatment

The patients were given the new EGCG formulation in 50 or 100 mg capsules, or placebo two to three times a day.

Assessment Criteria

Assessment was made from the frequency of relapses and duration of remission. A relapse was determined according to an increase in Crohn's disease activity index by 100 points over the basal level and provided that it held at a level above 150 points for two weeks.

Principal Results

Treatment with EGCG in 50 mg capsules reduced the frequency of relapses in comparison with placebo (28% and 69%, respectively; $p<0.001$).

Conclusion:

Treatment with EGCG in 50 mg capsules reduced the frequency of relapses and maintained remission in Crohn's disease cases when there were no clinical manifestations of the disease, even though blood had a high content of inflammation markers.

Example 9

Administration of EGCG to Women Having Hyperplastic Processes in the Endometrium (Adenomyosis)

The study involved 32 patients at an average age of 47.3±1.53 who refused to be given hormonal treatment and had no indications for surgery. The patients were taking 100 mg of EGCG twice a day for six months.

The efficiency of treatment was assessed three and six months later from clinical data and hormonal level, by ultrasonic scanning, separate diagnostic curettage, and paypel biopsy of the endometrium. The results are given in Table 3.

TABLE 3

Dynamics of Clinical Symptoms of Disease during Treatment with EGCG Preparations

| Symptoms | Before treatment, % | After 3 months of treatment, % | After 6 months of treatment, % |
|---|---|---|---|
| Menorrhagia (profuse menstruations) | 65.6 | 56.3 | 23.4 |
| Metrorrhagia | 46.9 | 28.1 | 15.6 |
| Pain in lower stomach related to the menstrual cycle | 28.1 | 18.8 | 15.6 |
| Pre- and post-menstrual blood discharges | 21.9 | 21.9 | 12.5 (scanty) |

Example 10

Study of the Prostate-Specific Antigen in the Blood of Patients Diagnosed with Prostate Cancer and Given the New EGCG Formulation The study involved 12 patients in the 1st and 2nd phases of prostate cancer. The diagnosis was confirmed by histological studies. The content of the prostate-specific antigen (PSA) in the blood of patients picked out for the study ranged between 12 and 20 ng/ml. The PSA was measured by the technique described by Jerry McLarty, Rebecca L. H. Bigelow, Mylinh Smith, et al. in their 2009 paper "Tea Polyphenols Decrease Serum Levels of Prostate-Specific Antigen, Hepatocyte Growth Factor, and Vascular Endothelial Growth Factor in Prostate Cancer Patients and Inhibit Production of Hepatocyte Growth Factor and Vascular Endothelial Growth Factor in vitro," *Cancer Prev. Res.*, 2 (7), 673-681).

The patients were taking the preparation in 100 mg doses three times a day for 30 days. The results of the study are given in Table 4.

TABLE 4

PSA Data during Treatment with EGCG Preparations

| Patients | PSA concentration (ng/ml) before treatment with the preparation | PSA concentration (ng/ml) after treatment with the preparation | Percent of PSA reduction |
|---|---|---|---|
| 1 | 12.3 | 3.7 | 30 |
| 2 | 18.5 | 6.3 | 34 |
| 3 | 16.4 | 5.2 | 32 |
| 4 | 12.3 | 5.0 | 40 |
| 5 | 16.8 | 5.5 | 33 |
| 6 | 12.5 | 4.3 | 34 |
| 7 | 13.8 | 5.4 | 39 |
| 8 | 14.6 | 4.4 | 30 |
| 9 | 12.7 | 4.0 | 31 |
| 10 | 19.5 | 7.8 | 40 |
| 11 | 12.6 | 4.5 | 36 |
| 12 | 17.9 | 7.0 | 39 |

What is claimed is:

1. A pharmaceutical composition for peroral administration containing epigallocatechin-3-gallate as an active component and a target additive, having a block copolymer of oxyethylene and oxypropylene as the target additive wherein the content of a hydrophobic block is less than 50% by mass and a hydrophilic block has a molecular weight of 2,250 daltons or more, at a weight ratio of the block copolymer to the active component ranging from 1:1 to 10:1.

2. The pharmaceutical composition of claim 1, further comprising Pluronic F127 as the block copolymer of oxyethylene and oxypropylene.

3. The pharmaceutical composition of claim 1, which is a dried, powder.

4. The pharmaceutical composition of claim 1, further comprising a pharmaceutically acceptable carrier.

5. The pharmaceutical composition of claim 4, which is in the form of a tablet, or dried powder, or suspension, or a capsule.

6. A method of administration of the pharmaceutical composition of claim 1 for treating atopic dermatitis, Crohn's disease, adenomyosis, and hyperplastic diseases of the prostate gland.

* * * * *